United States Patent [19]
Hammond

[11] Patent Number: 4,610,244
[45] Date of Patent: Sep. 9, 1986

[54] BRACE FOR RESTRAINING SHOULDER

[76] Inventor: Stella J. Hammond, 1408 W. Cross St., Ypsilanti, Mich. 48197

[21] Appl. No.: 786,692

[22] Filed: Oct. 11, 1985

[51] Int. Cl.$^4$ .............................................. A61F 5/00
[52] U.S. Cl. ..................................... 128/77; 128/134
[58] Field of Search ................... 128/94, 133, 134, 77

[56] References Cited
U.S. PATENT DOCUMENTS

| | | | |
|---|---|---|---|
| 3,010,452 | 11/1961 | Smith | 128/133 |
| 3,188,090 | 6/1965 | Job | 128/134 X |
| 3,324,851 | 6/1967 | Posner | 128/134 |
| 3,785,371 | 1/1974 | Lewis | 128/77 |
| 3,970,316 | 7/1976 | Westmoreland, Jr. | 128/134 X |
| 4,061,340 | 12/1977 | Husted | 128/134 X |
| 4,214,579 | 7/1980 | Ford | 128/94 |
| 4,327,909 | 5/1982 | Neufeld | 128/94 X |
| 4,337,938 | 7/1982 | Rodriguez | 128/94 X |

FOREIGN PATENT DOCUMENTS 8203596 4/1983 Netherlands ....................... 128/133

*Primary Examiner*—Sheldon J. Richter
*Attorney, Agent, or Firm*—Janine J. Weins; Michael J. Weins

[57] ABSTRACT

The shoulder brace of the present invention limits motion of the shoulder. The brace is comprised of a body belt, two arm belts and a resilient belt. The body belt is fastened about the torso. The first arm belt attaches about the upper arm while the second arm belt attaches about the fore arm. The resilient belt has a first end and a second end. The first end is attached to the body belt. Means are provided for connecting the second end of the resilient belt to the first arm belt and the second arm belt. Thus the resilient belt provides feedback when movement of the arm away from the torso is approaching the limit of movement permitted by the brace. If adjustment means to the resilient belt, such as a buckle, are provided it is possible to vary the range of permitted movement of the arm with respect to the torso.

11 Claims, 4 Drawing Figures

BRACE FOR RESTRAINING SHOULDER

FIELD OF INVENTION

The present invention relates to a body brace and more particularly to a brace that curtails the extent of the motion of the shoulder and upper arm.

BACKGROUND OF INVENTION

Prior art clavicle, arm and/or shoulder braces either substantially eliminate movement, or offer restriction to one or more components of motion, such as rotation of the shoulder.

Clavicle braces, such as those taught in U.S. Pat. No. 4,198,964 of Robert W. Honneffer and entitled: "ACROMIOCLAVICULAR BRACE"; U.S. Pat. No. 4,188,994 of Marian Z. Augustyniak and entitled: "ACROMIO-CLAVICULAR RESTORATION BRACE"; U.S. Pat. No. 3,499,441 of K. F. Hall entitled: "CLAVICLE BRACE", have shoulder pads which apply pressure to the clavicle bone and thus provide a force on the clavicle which in turn holds the acromioclavicular joint in location.

U.S. Pat. No. 4,446,858 of Verter entitled "ARM AND SHOULDER BRACE" teaches a brace which restricts movement of the arm and shoulder for stroke or accident victims who lack muscle tone or ligament integrity. This brace, like clavicular braces, is worn over the shoulder.

SUMMARY OF INVENTION

An object of this invention is to provide a brace which limits without eliminating mobility of the shoulder.

Another object of the invention is to provide a brace which provides increased resistance to movement as the limit of acceptable motion is approached.

Still another object of the invention is to provide a brace which is soft, pliable, comfortable.

The brace of the present invention in its simplest form has a body belt, two arm belts, and a resilient strap. The body belt is fastened about the torso. The first arm belt attaches about the upper arm. The second arm belt attaches about the forearm. The resilient strap has a first end and a second end. The first end is attached to the body belt. Means are provided for connecting the second end of the resilient strap to the first arm belt and to the second arm belt.

LIST OF FIGURES

BEST MODE FOR CARRYING THE INVENTION INTO PRACTICE

Figure 1:
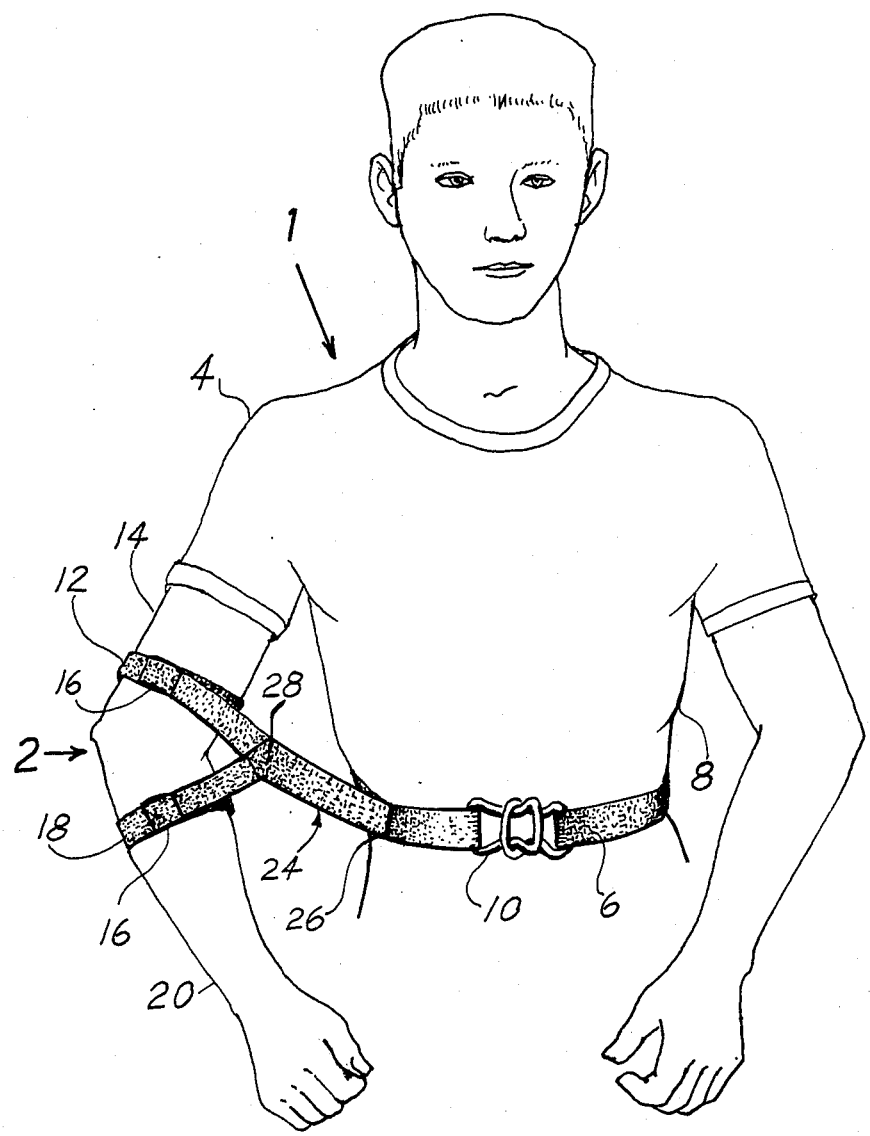
FIG. 1 is a schematic representation of an individual wearing the brace of the present invention.

FIG. 1 illustrates a brace of the present invention being worn by a person 1. The brace limits the mobility of arm 2 and shoulder 4. The brace of the present invention is comprised of four belt members.

A body belt 6 is worn about the torso 8. The body belt 6 is secured to the torso 8 by fastening means 10, such as a buckle. The body belt 6 may be either a separate belt or may be made an integral part of clothing such as a vest. The surface of the body belt 6 in contact with the torso 8 should be a non-slip material, such as a pile, so as to minimize the tendency of the body belt 6 to rotate about the waist of the wearer in response to motion of the arm 2 and shoulder 4.

A first arm belt 12 attaches to the upper arm 14. A second arm belt 18 attaches to the forearm 20. The first arm belt 12 and the second arm belt 18 may be a continuous segment which is formed as a figure eight. The arm belts may be fastened about the arm 2 using fastening means 16, such as a buckle, or a hook and pile type closure such as VELCRO TM.

A resilient belt 24 has a first end 26 which attaches to the body belt 6 and a second end 28 which is connected to the first arm belt 12 and the second arm belt 18. Typically the length of the resilient belt 24 is between about 4 inches and 8 inches depending on the height of the wearer and the restriction of motion sought. A buckle, ring, or an eye and hook can be used, for example, to connect the resilient belt 24 to the body belt 6. It is preferred to use a ring since the ring provides greater freedom of motion for the resilient belt 24 with respect to the body belt 6. If it is desired to vary the permitted extension of the arm, it is preferred to use a buckle or other adjustable means to attach resilient belt 24 to the body belt 6. The resilient belt 24 may be made of either a rigid or an elastic material depending on the degree of motion it is desired to have the shoulder brace of the present invention permit. When an elastic material is chosen it is preferred that the material allow for approximately 20% to 40% extension in length.

Figure 4:
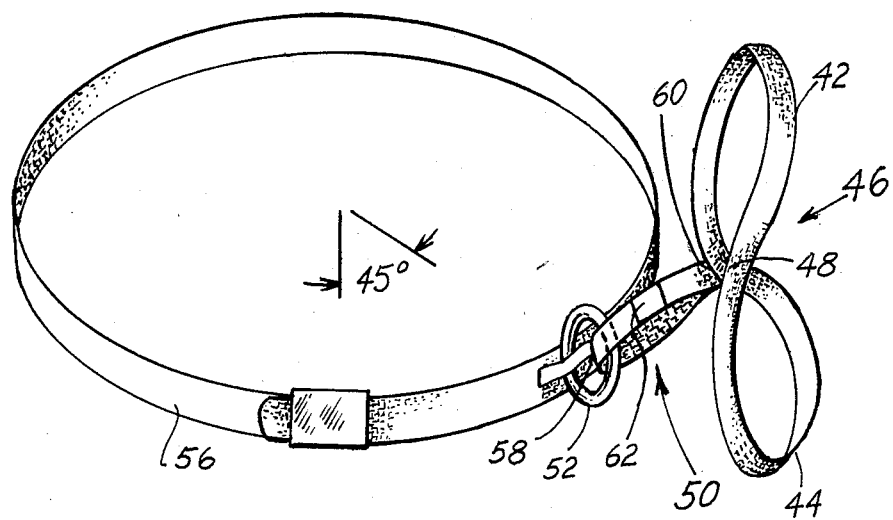
FIG. 4 illustrates an embodiment of the present invention in which means are provided for adjusting the extension of the arm with respect to the body and for limiting backward mobility of the arm and shoulder.

When it is desired to limit the backward motion of the shoulder it is preferred that the resilient belt 24 be attached to the body belt 6 at a position having a circumferential displaced from the belt buckle when such is worn in its normal position, of approximately 45°, as shown in FIG. 4. Attaching the first end 26 of the resilient belt 24 to the body belt 6 at a position approximately midway between the front center of the body and the position the arm would rest against the body in a relaxed manner, limits the backward motion of the shoulder.

When the brace of the present invention is worn as described above and shown in FIG. 1, movement of the shoulder 4 is restricted by the resilient belt 24. As the arm 2 is moved away from the body the tension applied to the arm 2 by the resilient belt 24 increases until the resilient strap becomes taut and further movement of the arm is not permitted. Thus resilient belt 24 provides feedback when movement of the arm 2 away from the torso is approaching the limit of movement permitted by the brace. The elasticity of the resilient strap will determine the characteristics of the feedback. If adjustment means to the resilient belt 24, such as a buckle, are provided it is possible to vary the range of permitted movement of the arm 2 with respect to the torso 8.

Figure 2:
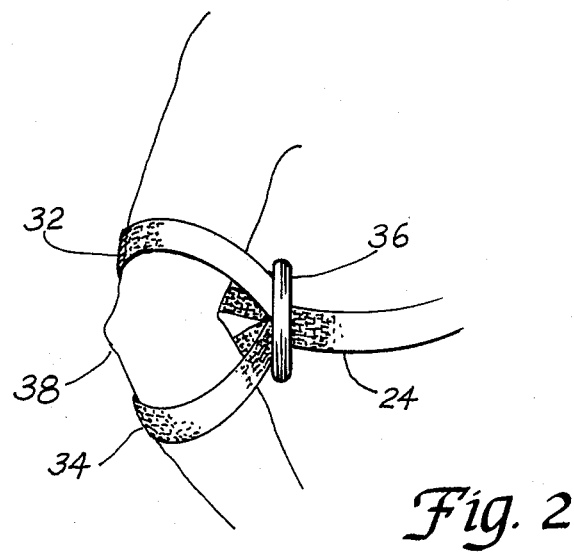
FIG. 2 illustrates a means employing a rigid straight spacer for connecting the resilient belt to the arm belts.

FIG. 2 illustrates an embodiment of the present invention in which a first arm belt 32 and a second arm belt 34 slip over the arm 2. A rigid spacer 36 is placed between and attached to the first arm belt 32 and the second arm belt 34 to assure separation of the first arm belt 32 and the second arm belt 34 and thus aids in maintaining the belts symmetrically disposed about the elbow 38. It is preferred that the spacer 36 is attached to the first arm belt 32 and the second arm belt 34 in such a manner as to provide a separation between the first arm belt 32 and the second arm belt 34 of about 0.1 and 1 inches. It has been found that when the arm belts are so separated the brace is more comfortable than when the arm belts are directly connected to the resilient belt 24. The rigid spacer 36 serves as a means for connecting the arm belts 32 and 34 to the resilient belt 24.

Figure 3:
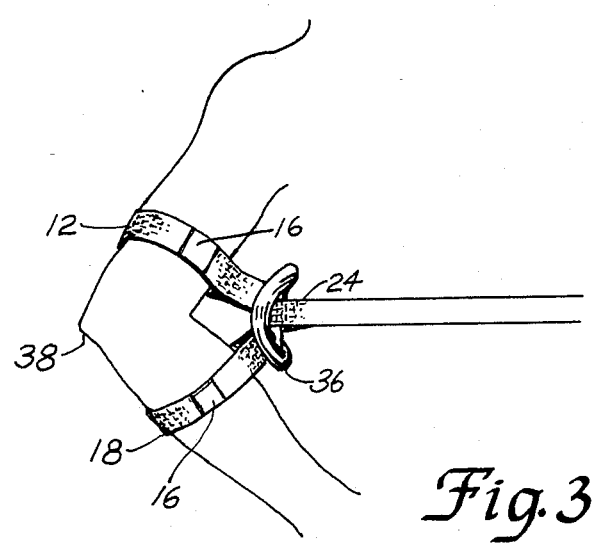
FIG. 3 illustrates a means employing a curved spacer for connecting the resilient belt to the arm belts.

FIG. 3 illustrates another embodiment of the present invention in which a first arm belt 12 and a second arm belt 18 are provided with fastening means 16 such as a snap, buckle, or a hook and pile type closure such as VELCRO ™. The fastening means allow the brace of the present invention to be readily worn over clothing, and to be attached to the arm with a minimum of disturbance to the arm. The first arm belt 12 and the second arm belt 18 are connected to the resilient belt 24 by means of a curved spacer 36 which has a preferred radius of curvature R between about 0.5 and 2 inches. The curvature allows for greater mobility of the elbow 38.

FIG. 4 illustrates an embodiment of the present invention in which a first arm belt 42 and a second arm belt 44 are continuous and are formed by crossing a large loop 46 to form a figure eight. A resilient strap 50 is attached to the first arm belt 42 and a second arm belt at the point of crossover 48. The strap 50 is preferably elastic. The resilient strap 50 forms a loop and said loop passes through a ring 52 which is affixed to the body belt 56. The contact point 58 of the ring 52 constitutes a first end for the resilient strap 50. The resilient strap 50 attaches to the first arm belt 42 and the second arm belt 44 at the point of crossover 48. This connection forms the second end 60 of the resilient strap 50. A clasp 62 is optionally provided to the resilient strap 50 so that adjustments can be made in the separation between the body belt 56 and the crossover 48. The clasp 62 can be any of a variety of adjustable means such as a buckle or a hook and pile type fastener such as VELCRO ™.

While the novel features of this invention have been described in terms of preferred embodiments and particular applications, it will be appreciated that various omissions and substitutions may be made by those skilled in the art without departing from the spirit of the invention.

What I claim is:

1. A shoulder brace, worn about a person's arm and torso to limit the mobility of the shoulder of the person comprising:

a body belt with fastening means attached about the torso;
    a first arm belt attached about the upper arm;
    a second arm belt attached about the forearm;
    a resilient strap having a first end and a second end, said first end being attached to said body belt; and
    and means for connecting said second end to said first arm belt and said second arm belt.

2. The shoulder brace of claim 1 wherein said means for connecting said second end arm belt further comprises:

a spacer, said spacer being attached to said first arm belt and to said second arm belt and providing an intermediate space therebetween.

3. The shoulder brace of claim 2 wherein said intermediate space is between about 0.1 inches and 1 inches.

4. The shoulder brace of claim 3 wherein said spacer is rigid.

5. The shoulder brace of claim 4 wherein said spacer forms a concave curve with a maximum radius of about 2 inches and said second end of said resilient strap being attached to said concave curve.

6. The shoulder brace of claim 5 further comprising:

a first fastening means for attaching said first belt; and
    a second fastening means for attaching said second belt.

7. The shoulder brace of claim 6 wherein said body belt attaching means is a buckle and said first and said second arm belt fastening means are a hook and pile type closure.

8. A shoulder brace, worn about the arm and torso of a person so as to limit the mobility of the shoulder of the person comprising:

a belt loop having a crossover so as to form a figure eight configuration having a first loop forming a first arm belt for attaching about the upper arm, and a second loop for attaching about the forearm;
    an elastic strap attached to said crossover; and
    a body belt attached to said elastic strap.

9. The shoulder brace of claim 8 wherein said elastic strap forms a loop and further comprising a ring for attaching said elastic strap to said body belt wherein said ring is affixed to said belt and said elastic loop passes through said ring.

10. The shoulder brace of claim 9 wherein said elastic strap is provided with means for adjusting the length of said elastic strap.

11. The shoulder brace of claim 10 wherein said means for adjusting the length of said elastic strap is a hook and pile type closure.

* * * * *